United States Patent [19]
Krüger et al.

[11] Patent Number: 5,256,682
[45] Date of Patent: Oct. 26, 1993

[54] ISOXAZOLYLIMIDAZOLE DERIVATIVES, PROCESS FOR THEIR PRODUCTION AND THEIR USE IN PHARMACEUTICAL AGENTS

[75] Inventors: Martin Krüger; Rolf Russe; Herbert Schneider; Ralph Schmiechen; Lechoslaw Turski, all of Berlin, Fed. Rep. of Germany

[73] Assignee: Schering Aktiengesellschaft, Berlin and Bergkamen, Fed. Rep. of Germany

[21] Appl. No.: 866,644

[22] Filed: Apr. 13, 1992

[30] Foreign Application Priority Data

Apr. 12, 1991 [DE] Fed. Rep. of Germany ....... 4112451

[51] Int. Cl.[5] .................. A61K 31/42; A61K 31/425; A61K 31/505; A61K 31/495
[52] U.S. Cl. .................... 514/378; 514/380; 514/369; 514/341; 514/269; 514/255; 514/252; 548/243; 548/247; 548/248; 548/182; 548/183; 548/184; 548/190; 548/191; 546/276; 544/298; 544/300; 544/310; 544/315; 544/316; 544/317; 544/405; 544/238
[58] Field of Search ............... 548/243, 247, 248, 182, 548/183, 184, 190, 191; 514/378, 380, 369, 341, 269, 255, 252; 546/276; 544/298, 300, 310, 315, 316, 317, 405, 238

[56] References Cited

U.S. PATENT DOCUMENTS 4,987,146 1/1991 Rohde et al. .................. 548/243
5,151,441 9/1992 Mueller et al. ................ 548/248

Primary Examiner—Mary C. Lee
Assistant Examiner—Joseph K. McKane
Attorney, Agent, or Firm—Millen, White, Zelano & Branigan

[57] ABSTRACT

4-Isoxazolyl-imidazole derivatives of formula I

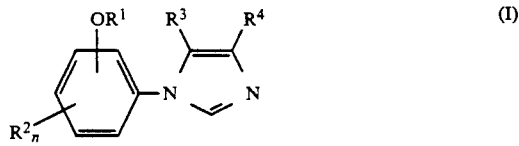

in which $R^1$, $R^2$, $R^3$ and $R^4$ have the meanings indicated, as well as their production and use in pharmaceutical agents, are described.

7 Claims, No Drawings

ISOXAZOLYLIMIDAZOLE DERIVATIVES, PROCESS FOR THEIR PRODUCTION AND THEIR USE IN PHARMACEUTICAL AGENTS

BACKGROUND OF THE INVENTION

The invention relates to new isoxazolylimidazole derivatives, their production and use in pharmaceutical agents.

It is known from EP-A-323 799 that imidazole derivatives have affinity to the benzodiazepine receptors and have effects on the central nervous system.

SUMMARY OF THE INVENTION

Surprisingly, the imidazoles according to the invention are marked by a clearly improved metabolic stability, by which their use for the production of a pharmaceutical agent is enhanced.

The invention relates to imidazole derivatives of formula I

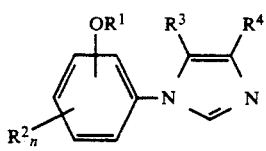

in which $R^1$ means hydrogen, an optionally substituted $C_{1-10}$ hydrocarbon or hetaryl radical or a cyclic ether radical, $R^2$ means hydrogen, halogen, an optionally substituted amino, nitro, azide, thiocyanate or cyano group, a straight or branched $C_{1-10}$ alkyl radical optionally substituted with halogen or an $-OR^1$ with $R^1$ in the meaning mentioned above and $R^2$ can be single or repeated and $R^1$ and $R^2$ together with the oxygen atom form a saturated or unsaturated 5- to 7-membered ring, which can also contain another heteroatom, and $R^3$ means hydrogen, a straight or branched $C_{1-6}$ alkyl group or a $C_{1-4}$ alkoxy-$C_{1-2}$ alkyl group and $R^4$ means

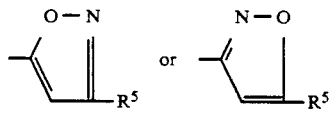

in which $R^5$ means hydrogen, $C_{1-6}$ alkyl, $C_{3-7}$ cycloalkyl, $C_{1-6}$ alkoxy, $C_{1-4}$ alkoxy-$C_{1-2}$ alkyl, $C_{2-6}$ alkoxycarbonyl, benzyl or phenyl, as well as their acid addition salts.

The substituents on the phenyl radical can be in o-, m- or p-position, and radical $R^2$ can occur 1-4 times especially singly or doubly and radicals $R^2$ and $-OR^1$ can be the same or different.

Halogen is to be understood to mean fluorine, chlorine, bromine or iodine in all cases.

Suitable hydrocarbon radicals $R^1$ include saturated or unsaturated, straight-chain or branched, optionally substituted alkyl groups with preferably up to 6 carbon atoms and, further, saturated or unsaturated cycloalkyl groups or cycloalkylalkyl groups with preferably 3 to 7 carbon atoms each, in which a $CH_2$ group is optionally replaced by an oxygen atom to form the mentioned cyclic ethers, as well as optionally substituted aryl or aralkyl groups with at most 10 carbon atoms.

As saturated, straight-chain or branched alkyl radicals throughout Formula I, the lower alkyl radicals such as methyl, ethyl, propyl, i-propyl, butyl, sec-butyl, isobutyl, tertbutyl as well as pentyl, hexyl, 2-methylbutyl, 2,2-dimethylpropyl are preferably meant. As unsaturated alkyl groups $R^1$ (i.e., alkenyl or alkynyl groups), the following alkenyl and alkynyl radicals can be mentioned as preferred: 1-propenyl, 2-propenyl, 3-methyl-2-propenyl, 2-propynyl. As a substituent of the alkyl groups $R^1$, halogen, such as especially fluorine, chlorine or bromine, hydroxy, $C_{1-4}$ alkoxy and amino, which optionally is monosubstituted or disubstituted by lower alkyl groups (e.g., 1-6 C atoms), are suitable. If fluorine is present as a substituent, the perfluoroalkyl compound is preferred. The foregoing also applies to the halo substituents on $R^2$. Cycloalkyl radicals are to be understood to mean preferably saturated radicals, such as, for example, cyclopropyl, cyclobutyl, cyclopentyl, cyclohexyl, cycloheptyl. As a suitable unsaturated radical, for example, cyclopentenyl can be mentioned.

If the hydrocarbon radical is a cycloalkylalkyl group, the cyclopropylmethyl, cyclopropylethyl and cyclopentylmethyl groups are preferred.

Suitable cycloalkyl groups interrupted by an oxygen atom are, for example, the cyclic ether groups 3-tetrahydrofuranyl and 3-tetrahydropyranyl.

If the hydrocarbon radical is an aryl or aralkyl group, the latter can be singly to triply substituted, for example, with halogen, nitro, cyano, hydroxy, mercapto, $C_{1-4}$ alkyl, $C_{1-4}$ alkoxy, $C_{1-4}$ alkylthio, $C_{1-4}$ alkylsulfinyl, $C_{1-4}$ alkylsulfonyl or an amino group optionally monosubstituted or disubstituted with $C_{1-4}$ alkyl, acyl (e.g., $C_{1-6}$ alkanoyl) or sulfonyl.

If $R^2$ means an amino group, the latter can be monosubstituted or disubstituted with $C_{1-4}$ alkyl or $C_{1-4}$ alkanoyl.

As a preferred aryl radical, phenyl can be mentioned, which optionally is substituted singly or doubly with halogen or a cyano, nitro or optionally substituted amino group as described above, such as, for example, 2,4-dichlorophenyl, 2-cyanophenyl, 4-aminophenyl.

Aralkyl radicals $R^1$ can be straight or branched in the alkyl radical and optionally can be singly or doubly substituted in the aryl radical, preferably with halogen, $C_{1-4}$ alkoxy, $C_{1-4}$ alkyl or with optionally substituted amino as described above.

Ar—$C_{1-2}$ alkyls, which can be substituted in the aryl radical by 1 to 2 halogens, especially bromine or chlorine, such as, for example, benzyl, phenethyl, α-methylbenzyl, are preferred.

If $R^1$ is a heteroaromatic radical, the latter can be 5 or 6-membered and contain one to two heteroatoms, such as sulfur, nitrogen and/or oxygen and can be substituted with the substituents mentioned above for the aryl radical. Six-membered ring heteroaromatic hydrocarbons with one to two nitrogen atoms and five-membered ring heteroaromatic hydrocarbons with one to two oxygen, sulfur and/or nitrogen atoms, which can be substituted by halogen, such as, for example, pyridine, pyrimidine, pyrazine, pyridazine, furan, thiophene, pyrrole, imidazole, thiazole, are preferred.

If $R^1$ and $R^2$ together with the oxygen atom form a ring, the hydrocarbon bridge can contain 1-3 carbon atoms, such as, for example, methylene, ethylene, ethylidene, propylene and in addition, another heteroatom, preferably oxygen.

Preferred embodiments of substituent $R^5$ are hydrogen, $C_{1-4}$ alkyl, $C_{3-5}$ cycloalkyl, $C_{1-4}$ alkoxy-$C_{1-2}$ alkyl, and the definition of these $R^5$ substituents corresponds to the meanings mentioned for $R^1$ above, preferably wherein the alkyl or cycloalkyl radicals are saturated and not substituted.

Preferred embodiments for substituent $R^2$ are hydrogen or $OR^1$.

The physiologically compatible acid addition salts are derived from the known inorganic and organic acids, such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid, as well as from alkanesulfonic acids, such as, for example, methanesulfonic acid, ethanesulfonic acid, benzenesulfonic acid, p-toluenesulfonic acid, etc.

The compounds according to the invention have agonistic, inverse agonistic and antagonistic effects on the known properties of benzodiazepines and are suitable for human medicine because of their biological effectiveness as psychopharmaceutical agents, especially as anxiolytic agents. Whether a given compound is agonistic, inverse agonistic or antagonistic can be routinely determined by conventional screening tests.

The effect of the compounds of formula I on the central nervous system and their metabolic stability was determined by tests according to methods known in the art. The compounds according to the invention are distinguished not only by anxiolytic effectiveness but show a superior metabolic stability in comparison with the imidazoles known from EP-323 799, as can be seen in the following table in comparison with the known 4-(5-ethyl-1,2,4-oxadiazol-3-yl)-5-methyl-1-(3-phenoxyphenyl)-imidazole (A).

TABLE

Compound % Radical after incubation with mouse liver homogenate

| | |
|---|---|
| A | 31 |
| B | 95 |
| C | 71 |
| D | 100 |

A = 4-(5-ethyl-1,2,4-oxadiazol)-3-yl)-5-methyl-1-(3-phenoxyphenyl)-imidazole
B = 4-(3-ethyl-isoxazol-5-yl)-5-methyl-1-(3-phenoxyphenyl)-imidazole
C = 4-(5-ethyl-isoxazol-3-yl)-5-methyl-1-(3-phenoxyphenyl)-imidazole
D = 4-(3-methoxymethyl-isoxazol-5-yl)-5-methyl-1-(3-phenoxyphenyl)-imidazole The stability of the compounds was measured as follows:

The test substance (1 μg/50 μl of ethanol) was adjusted with 750 μl of Krebs-Henseleit-Ringer phosphate buffer to pH 7.3 and brought together with 750 μl of a liver homogenate at room temperature and mixed. 250 μl of this batch was removed for zero-point determination and the batch was incubated at 37° C. with continuous movement in a water bath. Aliquot parts of 250 μl are removed after 120 minutes, extracted with 3 ml of diethyl ether after 5 minutes of shaking, then centrifuged for 10 minutes under cooling, frozen, the ether is decanted and dried in a dry nitrogen stream. The residue is dissolved in each case in 200 μl of ethanol and the solution is analyzed with HPLC. The liver used was obtained from NMRI mice and homogenized after removal immediate in 4 parts of a 0.25 molar sucrose solution in a Potter-Elvehjem mixer. The homogenate was then filtered through linen and diluted with the same sucrose solution to 1:10 (weight: volume). Aliquot parts of the solution were stored at −18° C.

The results of this test are listed in the table, and the amount of test substance is indicated in % of the zero value, which was not catabolized from metabolizing enzymes of the liver.

Because of their pharmacological properties, the compounds according to the invention can be formulated into psychopharmaceutical preparations, for example, for enteral and parenteral use.

To use the compounds according to the invention as pharmaceutical agents, the latter are brought into the form of a pharmaceutical preparation, which in addition to the active ingredient for enteral or parenteral administration contains suitable pharmaceutical, organic or inorganic inert vehicles, such as, for example, water, gelatin, gum arabic, lactose, starch, magnesium stearate, talc, vegetable oils, polyalkylene glycols, etc.

The pharmaceutical preparations can be present in solid form, for example as tablets, coated tablets, suppositories, capsules or in liquid form, for example, as solutions, suspensions or emulsions. They further optionally contain auxiliary agents, such as preservatives, stabilizers, wetting agents or emulsifiers, salts to change the osmotic pressure or buffers.

For parenteral use, injection solutions or suspensions, especially aqueous solutions of active compounds in polyhydroxyethoxylated castor oil, are especially suitable.

As vehicle systems, surface-active auxiliary agents such as salts of bile acids or animal or vegetable phospholipids, but also mixtures of them as well as liposomes or their components, can also be used.

For oral use, tablets, coated tablets or capsules with talc and/or a hydrocarbon vehicle or binder, such as, for example, lactose, corn or potato starch, are especially suitable. The use can also take place in liquid form, such as, for example, as juice, to which a sweetener optionally is added.

The compounds according to the invention can be introduced in a dosage unit of 0.05 to 10 mg of active substance in a physiologically compatible vehicle.

The compounds according to the invention are useful in a dose of 0.1 to 300 mg/day, preferably 1–30 mg/day, analogously to diazepam as an anxiolytic agent.

The production of the compounds of formula I according to the invention takes place according to processes known in the art, for example, in that a) an aniline of formula II

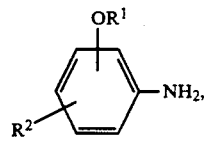

(II)

in which $R^1$ and $R^2$ have the meaning indicated in formula I, is reacted in the presence of acids with a 2-azadiene of formula III

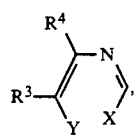

(III)

in which

R³ and R⁴ have the meaning indicated in formula I and

X and Y represent leaving groups or b) an imidazole derivative of formula IV

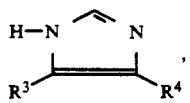
(IV)

in which R³ and R⁴ have the meaning indicated in formula I, is arylated with an aromatic hydrocarbon of formula V

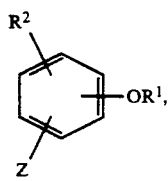
(V)

in which R¹ and R² have the meaning indicated in formula I and Z represents a leaving group, or c) an imidazole derivative of formula VI

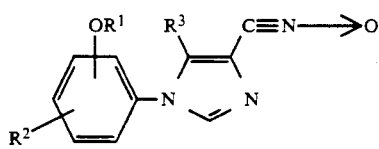
(VI)

in which

R¹, R² and R³ have the meaning indicated in formula I, is reacted with an acetylene derivative of formula VII

(VII)

in which

R⁵ has the meaning indicated in formula I, to an isoxazolylimidazole derivative of formula Ia

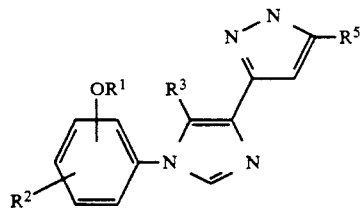
(Ia)

in which

R¹, R², R³ and R⁵ have the meaning indicated in formula I, or d) an imidazole derivative of formula VIII

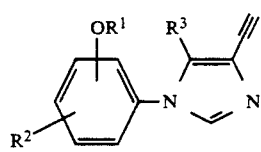
(VIII)

in which

R¹, R² and R³ have the meaning indicated in formula I, is reacted with a nitrile oxide of formula IX

$$R^5-C\equiv N\rightarrow O \quad (IX),$$

in which

R⁵ has the meaning indicated in formula I, to an isoxazolylimidazole derivative of formula Ib

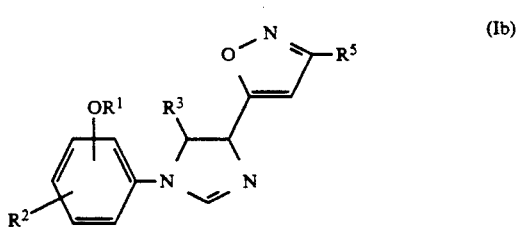
(Ib)

in which R¹, R², R³ and R⁵ have the meaning indicated in formula I, and optionally compounds with R¹=H are etherified in the presence of bases or a nitro group is reduced to the amino group and the latter is then optionally alkylated or acylated or exchanged for halogen, azide, cyano or thiocyanate or the acid addition salts are formed.

The reaction of anilines of formula II according to the invention with 2-azadienes of formula III to the imidazole derivatives of formula I takes place in the presence of acids at temperatures of 0 to 150° C. Leaving groups X and Y can be the same or different; $C_{1-3}$ dialkylamines, such as dimethylamine, diethyl amine and dipropylamine, and cyclic amines, such as pyrrolidine, are especially suitable.

The reaction is performed, for example, so that the aniline derivative and the azadiene in an organic acid, such as, for example, formic acid, acetic acid, propionic acid or trifluoroacetic acid, are first stirred at room temperature and then heated to the boiling temperature of the reaction mixture.

The acid can simultaneously be used as reactant and also as solvent. But solvents such as, for example, alcohols, ethers, ketones, esters, such as ethyl acetate, hydrocarbons, such as toluene or halogenated hydrocarbons, such as carbon tetrachloride, can also be added.

The amount of acid can be varied within wide limits, but it is used in excess. Preferably, a 3-10 times excess of acid, relative to the aniline and the azadiene, is selected.

The molar ratios of aniline and azadiene are not critical for the success of the reaction. In general, approximately the same molar amounts of the reactants are used, and quantitative ratios of 1 mol of aniline and 1-3 mol of azadiene are preferred. The reaction according to the invention can basically also be performed in the above indicated solvents with catalytic amounts of mineral acids, such as sulfuric acid, hydrochloric acid, perchloric acid or organic acids, such as p-toluenesulfonic acid and trifluoroacetic acid.

The advantage of the process of method a) according to the invention lies in the chemoselective synthesis of imidazole derivatives with the formation of only one isomer in a single process step.

The N-arylation of the imidazole derivatives of formula IV can take place, for example, according to the method described by N. W. Gilman et al., J. Heterocycl. Chem. 14, 1157 (1977). In this connection, it is necessary that the aromatic hydrocarbon of formula V is substituted with at least one electron-attracting group and with one leaving group. As electron-attracting groups, NO$_2$ and CN are especially suitable, and as leaving group Z, halogens, especially fluorine and iodine, are suitable. The arylation according to method b) is performed in the presence of bases such as alkali hydroxide, alkali hydride optionally in the presence of phase transfer catalysts, butyllithium or lithium diisopropylamide, preferably with alkali hydride.

For the reaction, temperatures of −78° C. to 100° C., preferably 0° C. to 50° C., are suitable.

As solvents for the arylation, aprotic polar solvents, for example, aliphatic and cyclic ethers such as diethyl ether, tetrahydrofuran, i.a. and dimethylformamide, are suitable.

The reaction of nitrile oxides of formula VI and IX with the acetylene derivatives of formula VII and VIII can take place, for example, according to the methods described by K. B. G. Torsell (K. B. G. Torsell, Nitrile Oxides, Nitrones and Nitronates in Organic Synthesis, 1988 VCH Verlagsgesellschaft mbH). In this way, as a rule, the nitrile oxide is first produced, which then is reacted without isolation with an acetylene derivative.

The molar ratios of nitrile oxide and acetylene can vary within wide limits. In general, approximately the same molar amounts of reactants are used, but it can often also be advantageous to use the acetylene derivative to a greater extent.

The reaction is performed in an aprotic solvent at temperatures of −78° C. to 150° C., preferably −20° C. to 50° C.

As solvents, for example, aliphatic and cyclic ethers, such as diethyl ether, tetrahydrofuran, dioxane, halogenated hydrocarbons, such as dichloroethane, methylene chloride, chloroform, hydrocarbons, such as hexane, pentane and dimethylformamide, dimethylsulfoxide, are suitable.

If the initial compounds are gaseous, such as, for example, acetylene, it is advantageous to use the corresponding liquid compounds, which have a subsequently easily cleavable group, in the reaction. As an easily cleavable group, for example, the trialkylsilyl group is suitable. The cleavage takes place before the working up of the reaction mixture according to the known methods, such as, for example, by adding bases at room temperature. Suitable bases are, for example, alkali hydroxides and alkali alcoholates, such as sodium hydroxide or potassium hydroxide, potassium methylate or ethylate, or fluorides, such as cesium fluoride or tetra-n-butyl-ammonium fluoride.

The advantage of the process of methods c) and d) according to the invention lies in the chemoselective synthesis of isoxazole derivatives with the formation of an isomer in a single step. The optionally subsequent etherification of compounds of formula I with $R^1$=H takes place according to methods known in the art. For example, a reactive derivative $R^1x$ can be reacted in a polar solvent in the presence of a base at temperatures from room temperature up to the boiling temperature of the solvent, optionally also in the presence of a phase transfer catalyst. As reactive radical X, halogen such as chlorine, bromine or iodine as well as the mesyl or tosyl group is especially suitable. As bases, alkali compounds such as sodium or potassium hydroxide, sodium or potassium carbonate, i.a., are suitable.

The reduction of the nitro group to the amino group can take place catalytically, for example, by being hydrogenated under standard pressure or H$_2$ pressure in polar solvents at room temperature. As catalyst, palladium can be used on a vehicle such as carbon or platinum in finely divided form; in compounds with halogen, preferably Raney nickel is used as catalyst. Polar solvents suitable for the reduction are, for example, alcohols or ethers, such as methanol, ethanol, diethyl ether, tetrahydrofuran or their mixtures.

The introduction of the cyano group can take place with the help of the Sandmeyer reaction; for example, the diazonium salts intermediately formed from the amino compounds with nitrites can be reacted with alkali cyanides in the presence of Cu-I-cyanide.

The introduction of the halogens chlorine, bromine or iodine by the amino group can take place, for example, according to Sandmeyer, by the diazonium salts intermediately formed with nitrites being reacted with Cu(I) chloride or Cu(I) bromide in the presence of the corresponding acid, hydrochloric acid or hydrobromic acid or being reacted with potassium iodide.

The introduction of fluorine is successful, for example, by Balz-Schiemann reaction of diazonium tetrafluoroborate.

The introduction of the azido or thiocyanate group can also take place by Sandmeyer reaction of the diazonium salt with alkali azide or alkali thiocyanate.

If an alkylation or acylation of the amino group is desired, it can be alkylated or acylated according to the usual methods, for example, with alkyl halides or acyl halides.

For the formation of physiologically compatible acid addition salts, a compound of formula I is dissolved, for example, in a little alcohol and mixed with a concentrated solution of the desired acid.

Insofar as the production of the initial compounds is not described, the latter are known or can be produced analogously to known compounds or processes described here. For example, the synthesis of 2-azadienes takes place according to Liebigs Ann. Chem. 1980, 344, and Liebigs Ann. Chem. 1986, 1749.

Nitrile oxides of formula VI and IX can be produced, for example, according to EP-A-305 322 and according to K. B. G. Torsell Nitrile Oxides, Nitrones and Nitronates in Organic Synthesis 1988. The acetylenes of formula VIII used as initial substances are mainly known or can be produced, for example, according to L. Brandsma, Preparative Acetylenic Chemistry, Second Edition, 1988.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application Federal Republic of Germany P 41 12 451.0 filed Apr. 12, 1992, are hereby incorporated by reference.

PRODUCTION OF 2-AZADIENES

Azadiene 1 a) 3-Ethyl-5-(N-dimethylaminomethylenaminomethyl)-isoxazole 9 g of 5-aminomethyl-3-ethyl-isoxazole is stirred in 12 ml of dimethylformamide-dimethylacetal with exclusion of moisture for 8 hours at 80° C. (bath temperature). After distillation on a bulb tube at 145° C. and 0.03 torr, 12.8 g (98% of theory) of the desired product is obtained.

b)
(E,Z)-1-Dimethylamino-3-(3-ethyl-isoxazol-5-yl)-4-(1-pyrrolidinyl)-2-azaoenta-1,3-diene 12.7 g of 3-ethyl-5-(N-dimethylaminomethylenaminomethyl)isoxazole, 11.4 ml of dimethylacetamide-dimethylacetal 90% and 5.8 ml of pyrrolidine are stirred for 24 hours at 80° C. (bath temperature). 4.17 g (21% of theory) of the formed product is obtained by bulb tube distillation at 210° C. to 220° C. and 0.1 torr.

Azadiene 2 a) 3-Methoxymethyl-5-(N,N-dimethylaminomethylenaminomethyl)isoxazole

The synthesis takes place according to azadiene 1a).

b) (E,Z)-1-Dimethylamino-3-(3-methoxymethyl-isoxazol-5-yl)-4(1-pyrrolidinyl)-2-azaoenta-1,3-diene The synthesis takes place according to azadiene 1b).

EXAMPLE 1 a)
4-(3-Ethyl-isoxazol-5-yl)-5-methyl-1-(3-phenoxyphenyl)imidazole 3.6 g of azadiene 1 is dissolved under cooling in 12 ml of glacial acetic acid and stirred for 15 minutes at room temperature. Then, 2.2 g of 3-phenoxyaniline is added and the mixture is stirred for 48 hours at room temperature and for 3 hours at 100° C. The glacial acetic acid is distilled off and the residue is mixed with NaHCO$_3$ solution and extracted with ethyl acetate. The crude product is purified by column chromatography. 1.53 g (37% of theory) of the title compound with a melting point of 97° C. (isopropyl ether) is obtained.

Analogously to example 1a), there were obtained:

b)
4-(3-Methoxymethyl-isoxazol-5-yl)-5-methyl-1-(3-phenoxyphenyl)-imidazole by reaction of azadiene 2; melting point 83° C. (isopropyl ether)

c)
4-(3-Ethyl-isoxazol-5-yl)-5-methyl-3-(4-chlorophenoxy)phenyl]-imidazole by reaction with azadiene 1 as oil.

EXAMPLE 2 a)
5-Methyl-1-(3-phenoxyphenyl)-imidazole-4-carbaldehyde 4.13 g of 5-methyl-1-(3-phenoxyphenyl)-imidazole-4-carbonitrile is dissolved in 200 ml of toluene. At −60° C. to −70° C., 15 ml of Dibah, 1.2 mol in toluene is instilled. It is stirred for 2 hours at −70° C., 2.5 ml of water is instilled at −70° C. and the mixture is allowed to come to room temperature. It is adjusted to pH 4 with 2N hydrochloric acid solution and the mixture is extracted with toluene and ethyl acetate. The organic phases are combined and dried on MgSO$_4$. After purification by column chromatography, 2.46 g (59% of theory) of the title compound is obtained as oil.

b)
5-Methyl-1-(3-phenoxyphenyl)-imidazole-4-carbaldehydoxim, hydrochloride 2.23 g of 5-methyl-1-(3-phenoxyphenyl)-imidazole-4-carbaldehyde is dissolved in 60 ml of ethanol and mixed with 0.70 g of hydroxylammonium chloride. The mixture is stirred for 2.5 hours at 80° C. (bath temperature). The solvent is distilled off and the residue is dissolved in 3 ml of ethanol. The product is crystallized out. 2.46 g (93% of theory) of the title compound with a melting point of 183° C. is obtained.

c)
4-(5-Methoxymethyl-isoxazol-3-yl)-5-methyl-1-(3-phenoxyphenyl)-imidazole 660 mg of 5-methyl-1-(3-phenoxyphenyl)-imidazole-4-carbaldehydoxime, hydrochloride is dissolved in 4 ml of dimethylformamide. At 0° C., 0.28 ml of triethylamine is added and a solution of 360 mg of N-bromosuccinimide in 2 ml of dimethylformamide is instilled within one hour. Then, 1.7 ml of methyl propargyl ether and 0.28 ml of triethylamine are added, and the mixture is stirred for 14 hours at room temperature. 360 mg of N-bromosuccinimide in 2 ml of dimethylformamide and 0.28 ml of triethylamine are again added and the mixture is stirred for 18 hours at room temperature. After the concentration by evaporation, it is mixed with water and extracted with ethyl acetate. The extract that has been concentrated by evaporation is mixed with diethyl ether and filtered. The filtrate is purified by column chromatography. 230 mg (32% of theory) of the title compound is obtained as oil.

Analogously to example 2c), there were obtained:

d)
4-(5-Ethyl-isoxazol-3-yl)-5-methyl-1-(3-phenoxyphenyl)imidazole by reaction with 1-butin; oil.

e)
4-(5-Ethyl-isoxazol-3-yl)-5-methyl-1-3-(4-chlorophenoxy)phenyl]-imidazole by reaction with 1-butin; melting point 95° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazole derivative of Formula I

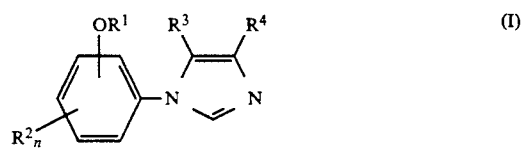

in which $R^1$ is hydrogen; a $C_1$–$C_{10}$-alkenyl or alkynyl radical optionally substituted by halogen, hydroxy, $C_1$–$C_4$ alkoxy or amino, which amino is optionally mono- or di-substituted by $C_1$–$C_6$ alkyl group(s); a $C_3$–$C_{10}$-cycloalkyl, cycloalkenyl, cycloalkylalkyl or cycloalkenylalkyl radical; or a hydrocarbyl aryl, hydrocarbyl aralkyl, isoxazolyl, pyridinyl, pyrimidinyl, pyrazinyl, pyridazinyl, furanyl, thiopheneyl, pyrrolyl, imidazolyl or thiazolyl radical each optionally mono- to tri-substituted with halogen, nitro, cyano, hydroxy, mercapto, $C_{1-4}$ alkyl, $C_{1-4}$ alkoxy, $C_{1-4}$ alkylthio, $C_{1-4}$ alkylsulfinyl, $C_{1-4}$ alkylsulfonyl or an amino group(s) which amino is optionally monosubstituted or disubstituted with $C_{1-4}$ alkyl, $C_{1-6}$ alkanoyl or sulfonyl groups(s); or a $C_{3-10}$ cyclic ether radical, $R^2$ is hydrogen, halogen, amino, which amino is optionally mono- or di-substituted with $C_1$–$C_4$ alkyl or $C_1$–$C_4$ alkanoyl group(s), nitro, azido, thiocyanato, cyano, $C_{1-10}$ alkyl optionally substituted with halogen or an —$OR^1$ group wherein $R^1$ is as defined above, n is 1–4 and each $R^2$ can be the same or different from the others, or $R^1$ and $R^2$ together with the oxygen atom from a 1 to 3 carbon bridge optionally containing a further oxygen heteroatom in the bridging chain, $R^3$ is hydrogen, $C_{1-6}$ alkyl or $C_{1-4}$ alkoxy-$C_{1-2}$ alkyl and $R^4$ is

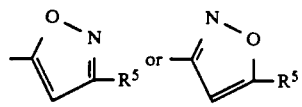

in which $R^5$ is hydrogen, $C_{1-6}$ alkyl, $C_{3-7}$ cycloalkyl, $C_{1-6}$ alkoxy, $C_{1-4}$ alkoxy-$C_{1-2}$ alkyl, $C_{2-6}$ alkoxycarbonyl, benzyl or phenyl or a pharmacologically acceptable acid addition salt thereof.

2. 4-(3-Ethyl-isoxazol-5-yl)-5-methyl-1-(3-phenoxyphenyl)-imidazole, 4-(3-methoxymethyl-isoxazol-5-yl)-5-methyl-1-(3-phenoxyphenyl)-imidazole, 4-(5-methoxymethyl-isoxazol-3-yl)-5-methyl-1-(3-phenoxyphenyl)-imidazole, 4-(5-ethyl-isoxazol-3-yl)    -5-methyl-1-(3-phenoxyphenyl)-imidazole, 4-(3-ethyl-isoxazole-5-yl)-5-methyl-[3-(4-chlorophenoxy)-phenyl]-imidazole, or 4-(5-ethyl-isoxazol-3-yl)-5-methyl-1-[3-(4-chlorophenoxy)-phenyl]-imidazole, each a compound of claim 1.

3. A compound of claim 1, in which $R^2$ is hydrogen.

4. A compound of claim 1 wherein n is 1 or 2.

5. A compound of claim 1, wherein $R^1$ is an alkyl, alkenyl, alkynyl, hydrocarbyl aryl or aralkyl radical.

6. A compound of claim 1 wherein $R^2$ is an $OR^1$ group.

7. A pharmaceutical agent comprising a compound of claim 1 and a pharmaceutically acceptable carrier.

* * * * *

UNITED STATES PATENT AND TRADEMARK OFFICE
CERTIFICATE OF CORRECTION

PATENT NO. : 5,256,682

DATED : October 26, 1993

INVENTOR(S) : Martin KRUGER et al.

It is certified that error appears in the above-identified patent and that said Letters Patent is hereby corrected as shown below:

Claim 1; Column 11; Line 1:

Insert after $C_1$-$C_{10}$ -- alkyl, --

Signed and Sealed this

Third Day of May, 1994

BRUCE LEHMAN

*Attest:*

*Attesting Officer*      *Commissioner of Patents and Trademarks*